United States Patent

Bateman et al.

[11] Patent Number: 4,794,252
[45] Date of Patent: Dec. 27, 1988

[54] DISCHARGE IONIZATION MASS SPECTROMETER

[75] Inventors: Robert H. Bateman, Knutsford; David S. Jones, Sale, both of England

[73] Assignee: VG Instruments Group Limited, Crawley, England

[21] Appl. No.: 72,019

[22] Filed: Jul. 10, 1987

[30] Foreign Application Priority Data

Jul. 11, 1986 [GB] United Kingdom ............... 8616940

[51] Int. Cl.⁴ .............................................. H01J 49/00
[52] U.S. Cl. ...................... 250/288; 250/281; 250/282
[58] Field of Search ............... 250/288 A, 288, 281, 250/423 R

[56] References Cited

U.S. PATENT DOCUMENTS 4,144,451  3/1979  Kambara ................. 250/281
4,160,161  7/1979  Horton .................... 250/283
4,647,772  3/1987  Lewis et al. ............. 250/288

Primary Examiner—Carolyn E. Fields
Assistant Examiner—John A. Miller
Attorney, Agent, or Firm—Chilton, Alix & Van Kirk

[57] ABSTRACT

The invention provides a mass spectrometer for the analysis of a sample dissolved in a fluid, and in particular a spectrometer for the analysis of high molecular weight compounds in the eluent of a liquid chromatograph. The fluid to be analyzed is at least partly vaporized and sprayed into the cathode dark space of a glow discharge. Ions characteristic of the sample are extracted from the discharge and subsequently mass analyzed. conveniently, spraying into the cathode dark space is achieved by making the cathode electrode of the discharge comprise the spraying means through which the fluid is sprayed. Little fragmentation of the high mass ions is caused by the process, and the invention extends the range of compounds which can be analyzed in comparison with similar prior art thermospray type mass spectrometers.

16 Claims, 3 Drawing Sheets

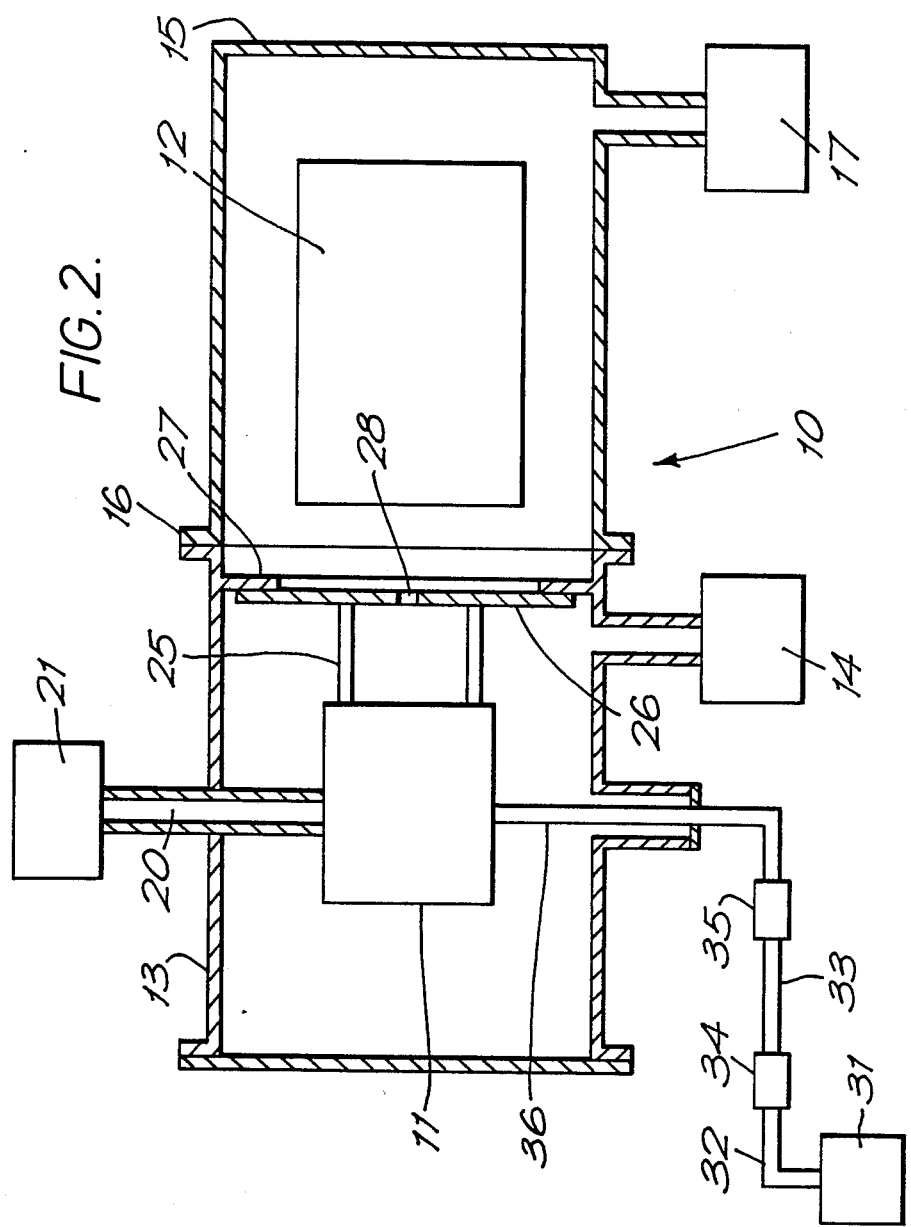

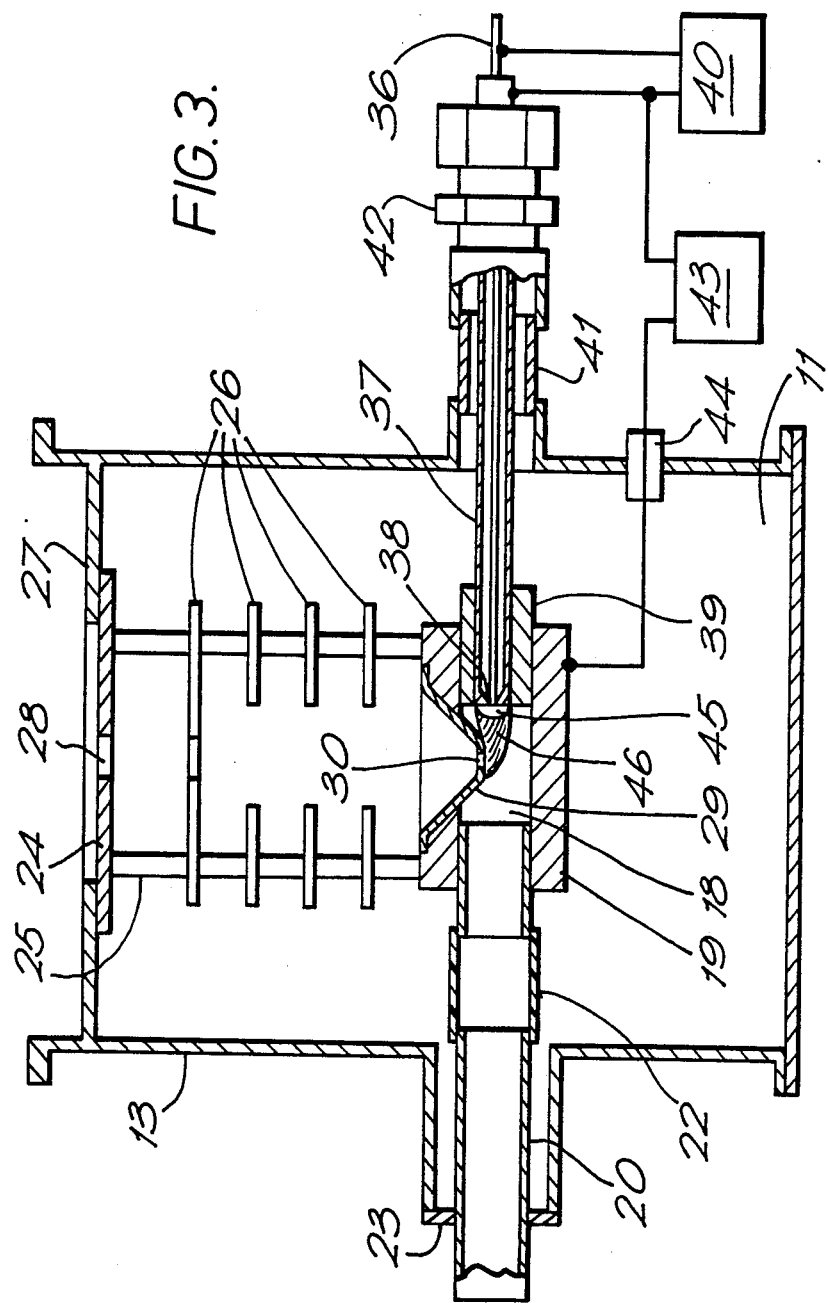

DISCHARGE IONIZATION MASS SPECTROMETER

This invention relates to a mass spectrometer adapted for the analysis of a sample dissolved in a solution in which ionization takes place in a glow discharge. In particular it relates to a mass spectrometer intended for the analysis of the eluent of a liquid chromatograph, especially using a "thermospray" type ion source. The term "thermospray" is used to describe the introduction of a fluid into a mass spectrometer ion source operating substantially below atmoshheric pressure through a spraying means which is typically heated so that the fluid emerges as a jet of fluid at least partly in the gas or vapour phase.

The first practical version of a thermospray type liquid chromatograph-mass spectrometer is described in International patent application publication number 81/03394. In the method, the eluent from the liquid chromatograph is passed through a capillary tube which is heated, typically to red heat, by means of four oxy-hydrogen torches, so that a jet of solvent vapour containing the sample is formed in a region of reduced pressure downstream of the end of the capillary tube. A conical skimmer containing a small hole in the centre is used to intercept the jet thus formed, and the vapour emerging through the hole (which contains a greater proportion of sample molecules) enters a tubular chamber, also maintained at a reduced pressure, where it impinges on a heated target situated downstream of the skimmer. An ion vapour is supposedly formed at this point and ions characteristic of the dissolved sample leave the tubular chamber through a hole in its wall adjacent to the heated target and are mass analyzed by a mass filter situated in a region of high vacuum. Surprisingly, the resultant mass spectra show no evidence of thermal decomposition,, even when thermally unstable samples are analyzed.

Later work by C. R. Blakley and M. L. Vestal, described in Analytical Chemistry, 1983, vol. 55, p. 750, showed that in fact the heated target could be omitted, and that ions were formed in the spray emerging from the heated capillary. The apparatus was further simplified by omission of the conical skimmer and the region of reduced pressure between it and the capillary nozzle. In this simplified version, the solution to be analyzed is pumped through a strongly heated capillary tube which protrudes into a wider bore tube maintained at a pressure of between 1 and 10 mbar by means of a mechanical vacuum pump. A spray of evaporating solvent droplets containing ions and molecules of the solvent is formed in the wider bore tube. A small hollow cone with a hole in its apex is positioned through the wall of the tube downstream of the end of the capillary with its axis at right angles to that of the spray and with its apex just short of the centre of the tube. The hole in the apex of the cone leads to the high vacuum part of the mass spectrometer, and ions passing through it enter the mass filter. The walls of the tube enclosing the spray and the sampling cone are advantageously heated. It is this type of mass spectrometer, with or without an additional ionization source, which is conventionally known as a thermospray mass spectrometer.

These thermospray methods are quite distinct from the earlier method of connecting a liquid chromatograph and a mass spectrometer in which the eluent is directly introduced in the liquid phase into the source of a conventional chemical ionization mass spectrometer, through a heated capillary, for example as described in U.S. Pat. No. 3,997,298. In ion sources of this kind, ionization of the sample is effected by reaction of the sample molecules with a plasma of ions formed from the solvent vapour by means of collisions with a beam of electrons inside the source. It is also distinct from liquid analyzing mass spectrometers based on techniques such as electrospray or electrohydrodynamic ionization, for example as described in U.S. Pat. Nos. 4,160,161, 4,209,696, and 4,144,451, in which ionization is effected by means of a high electrical potential applied between the capillary tube and a counter electrode situated opposite its end. In these systems a spray of charged droplets is generated as the liquid emerges from the capillary tube under the influence of the electrical field, and these droplets gradually evaporate leaving ions, usually clustered with solvent molecules, which are caused to pass through a hole in the counter electrode into a mass filter.

It is found that the optimum conditions for thermospray ionization occur when the liquid chromatograph eluent contains ions such as $NH_4^+$ and $CH_3COO^-$. Fortunately, mobile phases containing salts are commonly employed in the liquid chromatography of biochemicals, and consequently the method is very useful in this field.

However, in other cases, for example when the eluent comprises only a small amount of water and no buffers, the ionization process is found to be inefficient, and it is conventional to provide an external source of ionization, usually an electron beam, positioned so that it intersects the thermospray jet as it emerges from the nozzle and ionizes neutral molecules in the jet by a conventional electron- or chemical-ionization mechanism. For example, see Covey, T and Henion, J, Analytical Chemistry, 1983, vol 55 pp 2275-2280. It is also known to use a glow discharge as a source of ionization (Vestal, C. H., Garteiz, D. A., Smit, R., Blakley, C. R., paper presented at the 33rd An. meeting of the American Society for Mass Spectrometry, May 26-31st, 1983, San Diego, pp 771-712). FIG. 1 is a schematic drawing of such a prior type of thermospray ion source which uses a discharge. In FIG. 1, a heated block 1 comprises a conventional thermospray nozzle 2 and produces a jet 3 comprising neutral molecules of the sample. As in a conventional thermospray mass spectrometer, pump 4 is used to evacuate the thermospray chamber 5 and remove solvent molecules, and ions leave the jet through a hole in sampling cone 6 to enter a mass analyzer 7.

In order to improve the efficiency of the ionization of sample molecules in jet 3, a glow discharge is established between electrode 8 and the wall of chamber 5 by maintaining a potential difference of about 500-1000 volts between electrode 8 and the wall of chamber 5 by means of glow discharge power supply 9. The pressure of solvent vapour in chamber 5 will be between 0.1 and 10 mbar. dependent on the flow rate of liquid into the thermospray heated blook and the volatility of the solvent, so that a glow discharge can easily be struck in the solvent vapour between electrode 8 and the walls of chamber 5. Neutral molecules in the thermospray jet enter the region of glow discharge and are ionized, probably either by collision with free electrons or with metastable solvent molecules present in the discharge. It is found that the ionization process is surprisingly gentle, although it does result in slightly more fragmentation of the sample molecules than is the case with a thermospray ion source operated without any external ionization. Consequently, the technique can be used for the analysis of high molcular weight organic compounds and is therefore distinguished from the glow discharge sputtering sources incorporated in mass spectrometers adapted for the elemental analysis of solids, for example as described by Harrison W. W., Hes K. R., Marcus R. K. and King F. L., published in Analytical Chemistry, 1986, vol 58 (2), pp. 341A–336A. In spectrometers of this kind, ions present in the discharge sputter material from the cathode which is subsequently ionized in the discharge region and mass analyzed, whilst in the thermospray-discharge system, the discharge is used to ionize a jet of fluid and vapour containing the sample.

One problem encountered with the type of thermospray-discharge source illustrated in FIG. 1 is that it is essential for the discharge to be located in the path of the jet emerging from the nozzle in order for ionization to be effective. In practice it is found that as the flow of liquid is increased, the discharge itself becomes displaced and eventually becomes confined to the region surrounding the sides of electrode 8 where it no longer causes ionization of the jet. Further, the overall efficiency of the process is limited by the failure of a large proportion of the material to actually enter the discharge plasma, especially at high flow rates, so that the maximum potential sensitivity of the system cannot be realised.

It is the object of the present invention, therefore, to provide a fluid analyzing mass spectrometer comprising a discharge ionization source which has higher sensitivity than previously known versions and in which dependence of the ionization efficiency on the fluid composition and flow rate is substantially reduced.

According to one aspect there is provided a mass spectrometer adapted for the analysis of a sample dissolved in a fluid comprising:
(a) spraying means for spraying said fluid into a spraying chamber in the form of a jet of fluid at least partly in the gas or vapour phase;
(b) means for maintaining the pressure in said spraying chamber substantially below atmospheric pressure;
(c) means for creating and maintaining in said spraying chamber and between at least two electrode means, a glow discharge having a cathode dark space, in which discharge ions characteristic of said sample are formed; and
(d) means for extracting from said discharge and subsequently mass analyzing at least some of said ions;
the improvement in which said glow discharge is disposed adjacent to said spraying means and at least one of said electrode means comprises said spraying means.

Preferably, the fluid is a liquid, and means are provided for heating and at least partly vaporizing the liquid before it is passed into the spraying means.

According to another aspect the invention comprises a mass spectrometer adapted for the analysis of a solution containing a sample, comprising:
(a) means for heating said solution and passing it through a spraying means capable of thermospraying said solution into a spraying chamber;
(b) means for maintaining said spraying chamber substantially below atmospheric pressure;
(c) means for creating and maintaining in said spraying chamber and between at least two electrode means a glow discharge having a cathode dark space;
(d) means for mass analyzing at least some of the ions created in said discharge which are characteristic of said sample;
the improvement in which said glow discharge is adjacent to said spraying means and at least one of said electrode means comprises said spraying means.

Viewed from another aspect the invention comprises a method of analyzing a sample dissolved in a fluid comprising at least partly vaporizing said fluid and spraying it into a glow discharge having a cathode dark space and established in a region maintained at a pressure substantially below atmospheric pressure, extracting from said discharge at least some ions characteristic of said sample formed therein, and subsequently mass analyzing said ions, the improvement in said method comprising spraying said at least partly vaporized fluid directly into said cathode dark space.

Preferably the fluid is a liquid which is at least partly vaporized by heating prior to its being sprayed into the glow discharge.

According to yet another aspect, the invention provides a method of analyzing a sample dissolved in a solution, comprising:
(a) causing said solution to be heated and to flow through a spraying means;
(b) establishing in a region downstream of said spraying means a glow discharge having a cathode dark space;
(c) maintaining said region substantially below atmospheric pressure;
(d) thermospraying said solution from said spraying means into said region;
(e) forming within said discharge at least some ions characteristic of said sample; and
(f) extracting and subsequently mass analyzing at least some of said ions;
the improvement in said method comprising thermospraying said solution directly into said cathode dark space.

Preferably the electrode means comprise an anode and a cathode, with the cathode comprising the spraying means, and the anode comprising a conductive wall of the spraying chamber.

In this way, the sample contained in the fluid can be efficiently ionized without causing fragmentation of labile high molecular weight molecules. The exact mechanism of the process is not known, but it is probable that sample molecules are ionized by collision with neutral metastable species which have high translational energy and which are present in the cathode dark space. This process of ionization is similar to ionization by means of fast neutral atom bombarbment used in a conventional organic mass spectrometer adapted for the analysis of high molecular weight compounds, which is known to cause very little fragmentation of the molecules. In contrast, in the prior art thermospray-discharge mass spectrometer shown in FIG. 1, the sample molecules are ionized in the glow region of the discharge in which there exists a large concentration of relatively slow moving charged species, and ionization by collision with many of these is likely to be inefficient because of their low translational energies.

Preferably, the spraying means comprises a strongly heated capillary tube through which the fluid is pumped and which is adapted to produce a jet of liquid and vapour. Unionized molecules of the sample present in this jet enter the dark space of the discharge and are ionized, and these ions are subsequently mass analyzed using any suitable mass analyzer. In a preferred embodiment, the cathode electrode of the discharge comprises the spraying means which is usually the end of a heated capillary tube.

In order to operate the glow discharge, a potential difference of approximately 500 volts is applied between the two electrodes, which are typically the capillary tube and the walls of the spraying chamber, with the negative terminal of the supply connected to the spraying means. As in a conventional thermospray type ion source, the pressure in the spraying chamber, due mainly to solvent vapour, is typically between 1 and 100 mbar, and a current of 0.1-10.0 mA will flow between the electrodes. Preferably the power supply should be an adjustable voltage type, as the potential difference needed will be dependent on the nature of the solvent and the pressure in the spraying chamber. The discharge current is preferably adjusted to and subsequently maintained at a value at which the "normal" glow at least partly covers the cathode electrode.

Preferably also the spraying chamber itself is heated to prevent condensation of the solvent on its walls.

In prior types of thermospray mass spectrometers, the temperature of the heated capillary must be carefully selected to obtain optimum performance. However, an advantage of the present invention is that the capillary temperature need not be as as carefully selected or controlled. It has been found that the ionization process of the present invention is capable of causing efficient ionzation of sample molecules over a much wider range of liquid/vapour ratios in the spray than the prior type of thermospray ionization. Typically, a temperature of 180°±30° C. may be used for a solution of 50% water and 50% methanol flowing at 1 ml/min.

Other advantages of the invention over prior thermospray mass spectrometers include an increase in the maximum usable capillary diameter, which reduces the risk of blocking during operation, and the elimination of the need for buffered or aqueous solutions which are necessary for efficient thermospray ionization.

However, it will be appreciated that the spectrometer of the present invention can be used as a conventional thermospray spectrometer simply by switching off the glow discharge power supply and electrically connecting together the walls of the spraying chamber and the heated capillary.

Ions may be sampled from the discharge region by any suitable method. Typically. a sampling cone with a small hole at its apex is provided as in a thermospray ionization source. This is mounted downstream of the heated capillary through the wall of the spraying chamber with its axis substantially perpendicular to the axis of the capillary. The hole leads into a second chamber containing a suitable mass analyzer and which is maintained at a pressure of $10^{-4}$ mbar or lower.

Selection of the distance between the hole and the spraying means is important for efficient operation of the spectrometer. In general the optimum distance is approximately one-half of the optimum distance for a thermospray spectrometer. It is preferably adjusted to maximise transmission of ions characteristic of the sample from the spraying chamber into the mass analyzer. Conveniently, the distance that the capillary protrudes into the spraying chamber is made adjustable, so that the distance between the spraying means and the hole can be adjusted by moving the capillary. Sufficient range of adjustment is provided to allow the distance to be set for optimum operation in either the thermospray mode or the mode according to the invention. Typically, a distance of 3-6 mm is suitable.

Other ion sampling arrangements can be used to extract ions from the discharge, and it will be understood that the invention is not limited to a sampling cone disposed perpendicularly to the heated capillary.

Various types of mass analyzers may be employed in the invention, dependent on the mass range and resolution required. In the case of a quadrupole type of analyzer, the potential of the spraying chamber and sampling cone will be maintained at the ion energy of the analyzer, which is usually close to ground potential, so that the cathode electrode of the discharge (which comprises the spraying means) will be approximately $-500$ volts relative to ground. In the case of a magnetic sector mass analyzer, the spraying chamber and sampling cone will be maintained at the accelerating voltage of the analyzer, typically $+4$ to $+8$ KV for positive ions or $-4$ to $-8$ KV for negative ions, so that the potential of the spraying means will be about 500 volts lower than this. In the case when a liquid chromatograph is connected to the spectrometer, it is desirable that the chromatograph should be at ground potential. This may be achieved by the provision of a section of insulating pipe connecting the spraying means to the chromatograph. This may conveniently comprise a length of glass or quartz tubing. Obviously, when electrically conductive solutions are used there will be some electrical leakage from the discharge ion source to ground through the solution, but in practice this can be kept below 1 mA if a 40-50 cm long piece of glass capillary tubing is employed, even when an 8 KV accelerating potential is employed. Shorter lengths may be used when a quadrupole analyzer is being used.

A preferred embodiment of the invention will now be described in greater detail by way of example and by reference to the figures in which:

FIG. 2 is a simplified diagram of a mass spectrometer incorporating the invention; and FIG. 3 is a drawing of a discharge ionization source suitable for use in the spectrometer of FIG. 2.

Figure 1:
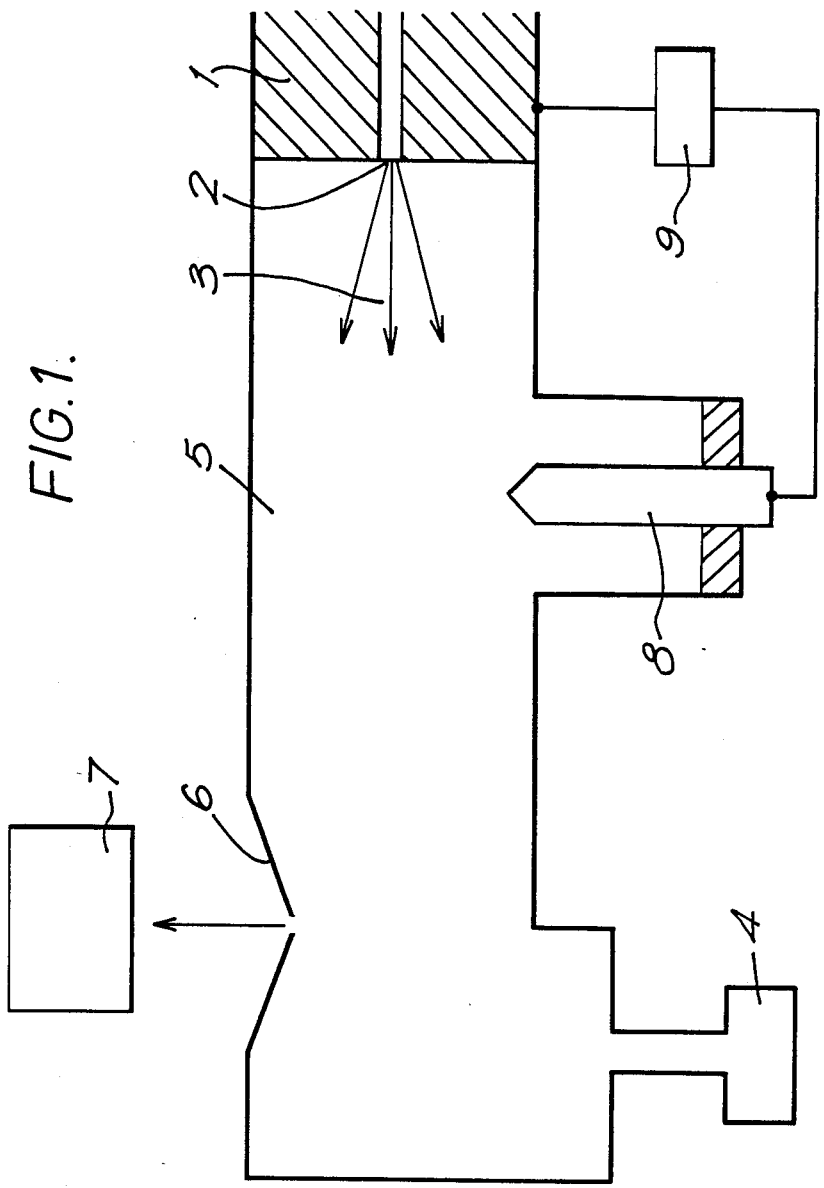
FIG. 1 illustrates a prior type of glow discharge-thermospray ion source, previously described.

Referring first to FIG. 2, a mass spectrometer 10 comprises a discharge ionization source 11 and a mass analyzer 12. Source 11 is contained in a housing 13 which is evacuated by a vacuum pump 14, capable of maintaining the pressure in housing 13 below $10^{-3}$ mbar. Analyzer 12 is contained within housing 15 which is attached to housing 13 by flanged joint 16. A vacuum pump 17 is used to maintain the pressure in housing 15 below $10^{-5}$ mbar. Mass analyzer 12 may comprise any conventional mass analyzer, for example, a quadrupole mass analyzer, high or low resolution magnetic sector analyzers, a time-of-flight mass analyzer, or an ion-cyclotron resonance spectrometer.

The discharge ionization source 11 is shown in greater detail in FIG. 3. It comprises a spraying chamber 18 and an ion block 19 which is evacuated through a large bore tube 20 by a mechanical vacuum pump 21 (FIG. 2). Pump 21 is of sufficient capacity to ensure that the pressure inside chamber 18 remains within the desired range during operation. In most cases, the potential of block 19 will not be ground, so that tube 20 also comprises a tubular insulator 22. Typically, tube 20 may be made from stainless steel about 10 mm diameter, and the insulator 22 may comprise PTFE tube. It is also desirable that a flexible portion is incorporated in tube 20 to allow for slight misalignment of its mounting port 23 on housing 13 and ion block 19. This is easily achieved when insulator 22 is a short section of PTFE tube. Alternatively, stainless steel tube 20 can be omitted, and insulating tube 22 can be extended through port 23 to connect directly to pump 21.

The ion block 19 is supported from a source mounting flange 24 by four source mounting rods 25. Each mounting rod comprises a solid ceramic rod over which a plurality of tubular ceramic spacers are fitted. The focusing and deflecting electrodes 26 are supported on rods 25 between these spacers.

Source mounting flange 24 is in turn mounted on a flange 27, welded to the inside wall of housing 13, and contains a small aperture 28 through which ions formed in source 11 pass into the mass analyzer 12. In the case when analyzer 12 is a magnetic sector analyzer, aperture 28 comprises a small rectangular slit which is typically 0.1×5 mm. Means, external to housing 13, may be provided for adjusting the width of the slit. In the case when analyzer 12 is a quadrupole analyzer, aperture 28 is typically a small round hole.

A sampling cone 29, containing in its apex a small aperture 30, (typically 0.3 mm diameter), is fitted into ion block 19 so that its apex protrudes into spraying chamber 18. Ions formed in chamber 18 leave through aperture 30 and are focused on to aperture 28 in mounting flange 24 by means of the electrical field created by electrodes 26. These electrodes are connected to suitable electrical supplies by means of feedthrough insulators (not shown) fitted in the wall of housing 13, and operate in a conventional way.

The fluid containing the sample to be analyzed, typically a liquid solution, is pumped by pump means 31 (FIG. 2) through capillaries 32 and 36 into the discharge ionization source 11. An insulating capillary 33, made typically from quartz, glass or PTFE, is inserted between capillaries 32 and 36 and connected to them by couplings 34 and 35. Capillary 36 operates at substantially the same electrical potential as ion block 19, so that insulated capillary 33 provides electrical insulation and permits pump means 31 to operate at ground potential. Typically, pump means 31 may comprise a liquid chromatograph, and in order to minimize broadening of the chromatographic peaks, the bore of capillaries 32, 33, and 36 should not be greater than 0.15 mm. In order to prevent excessive electrical leakage from block 19 to ground in the case when the potential of block 19 is several KV above ground and an electrically conductive solution is being analyzed, capillary 33 should be at least 10, and preferably at least 30 cm long.

Capillary 36 is fitted inside a larger bore tube 37 which is joined to the end of capillary 36 to form spraying means 38 inside chamber 18. Electrical insulator 39 seals tube 37 into ion block 19 and provides electrical insulation between them. Capillary 36 is heated by an electrical current passed through it via tube 37 from heater power supply 40. Preferably, capillary 36 and tube 37 are made from stainless steel.

Tube 37 is supported by a second electrical insulator 41 fitted in a port on housing 13 and by pipe coupling 42 as shown in FIG. 3. The distance between spraying means 38 and aperture 30 in sampling cone 29 is set by loosening the nut on pipe coupling 42 and sliding tube 37 in the coupling until the desired distance between spraying means 38 and aperture 30 is achieved, after which the nut is retightened. To facilitate this, the ferrule in coupling 42 is preferably made from PTFE. For optimum operation according to the invention the distance should be set to between 3 and 6 mm.

As explained, a glow discharge 46, having a cathode dark space 45, is established between at least two electrode means. Preferably two electrodes are provided, a cathode comprising spraying means 38 (formed by the ends of tube 37 and capillary 36), and an anode comprising the ion block 19. Glow discharge poeer supply 43 generates a suitable potential difference which is applied to capillary 36 (negative) and ion block 19 (positive), as shown in FIG. 3. Ion block 19 is connected to power supply 43 by means of feedthrough 44 in housing 13. It is also maintained at the accelerating voltage of the mass spectrometer, so that supplies 40 and 43 must be capable of floating at a potential of up to 8 KV above ground.

Typically, the glow discharge power supply 43 is capable of generating a potential of approximately 500 volts at a current of up to 10 mA. Typically, the pressure in the spraying chamber 18 will be 1–100 mbar, and a current of 0.1–10 mA will flow between the electrode means. Power supply 43 should preferably be an adjustable voltage type, as the potential difference required for optimum operation is dependent on the nature of the solvent and the pressure in the spraying chamber. The discharge current is adjusted to and maintained at a value such that the "normal" glow of the discharge at least partly covers the spraying means 38.

Heater power supply 40 is typically capable of delivering up to 20 A at a low potential difference, so that capillary 36 is heated to the required temperature. Typically, a power of approximately 150 W is suitable, but this will be dependent on the material used for the capillary and its cross-sectional area.

The temperature of the capillary 36 required for the most efficient operation is dependent on the fluid being analyzed, and on its flow rate. A temperature of 180±30° C. is typical for an aqueous solution. In general a temperature about 20° C. lower than the optimum temperature for thermospray ionization is most suitable, but the selection is best done by experiment to obtain the maximum transmission of sample ions into the mass analyzer.

The spectrometer of the invention can be operated in the thermospray mode when desired simply be turning off the glow discharge power supply 43. The distance between the aperture 30 and spraying means 38 is preferably increased to 5–10 mm by moving tube 37 in coupling 42, but there is a range (about 5–6 mm) which is reasonably efficient for both modes of operation. Selection of the remaining conditions is then made according to conventional thermospray practice.

What is claimed is:

1. In a mass spectrometer adapted for the analysis of a sample dissolved in a fluid comprising:
    (a) spraying means for spraying said fluid into a spraying chamber in the form of a jet of fluid at least partly in the gas or vapour phase;
    (b) means for maintaining the pressure in said spraying chamber substantially below atmospheric pressure;
    (c) means for creating and maintaining in said spraying chamber and between at least two electrode means a glow discharge having a cathode dark space in which discharge ions characteristic of said sample are formed; and (d) means for extracting from said discharge and subsequently mass analyzing at least some of said ions;

the improvement in which said discharge is disposed adjacent said spraying means and one of said electrode means comprises said spraying means.

2. A mass spectrometer according to claim 1 in which said fluid is a liquid and means are provided for heating and at least partly vaporizing said liquid before it is passed into said spraying means.

3. A mass spectrometer according to claim 2 in which said spraying means comprises a heated capillary tube for producing a jet of liquid and vapour.

4. In a mass spectrometer adapted for the analysis of a solution containing a sample comprising:
 (a) means for heating said solution and passing it through a spraying means for thermospraying said solution into a spraying chamber;
 (b) means for maintaining said spraying chamber substantially below atmospheric pressure;
 (c) means for creating in said spraying chamber and between at least two electrode means a glow discharge having a cathode dark space;
 (d) means for mass analyzing at least some of the ions created in said discharge which are characteristic of said sample;

the improvement in which said glow discharge is disposed adjacent said spraying means and at least one of said electrode means comprises said spraying means.

5. A mass spectrometer according to claim 1 in which said electrode means comprise an anode and a cathode, said cathode comprises said spraying means, said spraying means spraying fluid directly into said cathode dark space.

6. A mass spectrometer according to claim 2 in which said electrode means comprise an anode and a cathode, said cathode comprises said spraying means, said spraying means spraying fluid directly into said cathode dark space.

7. A mass spectrometer according to claim 2 in which means are provided for heating said spraying chamber.

8. A mass spectrometer according to claim 1 in which means are provided for adjusting the distance between the spraying means and the means for extracting ions from the discharge.

9. A mass spectrometer according to claim 8 in which said means for extracting ions comprises a sampling cone with a hole at its apex, and said distance is selected to optimize transmission of said ions through said hole into a mass analyzer.

10. A mass spectrometer according to claim 2 in which means are provided for adjusting the distance between the spraying means and the means for extracting ions from the discharge.

11. A mass spectrometer according to claim 10 in which said means for extracting ions comprises a sampling cone with a hole at its apex, and said distance is selected to optimize transmission of said ions through said hole into a mass analyzer.

12. A mass spectrometer according to claim 2 in which means are provided for maintaining the temperature of the spraying means at $180°\pm+°$ C. and the distance between the spraying means and the means for extracting ions is between 3 and 6 mm.

13. In a method of analyzing a sample dissolved in a fluid comprising at least partly vaporizing said fluid and spraying it into a glow discharge having a cathode dark space and established in a region maintained at a pressure substantially below atmospheric pressure, extracting from said discharge at least some of the ions characteristic of said sample formed therein, and subsequently mass analyzing said ions, the improvement in said method comprising spraying said at least vaporized fluid directly into said cathode dark space.

14. A method according to claim 13 in which said fluid is a liquid which is at least partly vaporized by heating prior to its being sprayed into said glow discharge.

15. In a method of analyzing a sample dissolved in a solution comprising:
 (a) causing said solution to be heated and to flow through a spraying means;
 (b) establishing in a region downstream of said spraying means a glow discharge having a cathode dark space;
 (c) maintaining said region substantially below atmospheric pressure;
 (d) thermospraying said solution from said spraying means into said region;
 (e) forming within said discharge at least some ions characteristic of said sample; and
 (f) extracting and subsequently mass analyzing at least some of said ions;

the improvement comprising thermospraying said solution directly into said cathode dark space.

16. The method of claim 15 including the step of connecting the spraying means to a source of electrical potential wherein the spraying means will function as a cathode of said glow discharge.

* * * * *